United States Patent
Lading et al.

(10) Patent No.: US 10,039,455 B2
(45) Date of Patent: Aug. 7, 2018

(54) CONTINUOUS CALIBRATION OF A BLOOD PRESSURE MEASUREMENT DEVICE

(71) Applicant: QUALCOMM Incorporated, San Diego, CA (US)

(72) Inventors: Lars Lading, Roskilde (DK); David Boettcher Baek, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 219 days.

(21) Appl. No.: 14/714,966

(22) Filed: May 18, 2015

(65) Prior Publication Data

US 2015/0327785 A1 Nov. 19, 2015

Related U.S. Application Data

(60) Provisional application No. 62/000,078, filed on May 19, 2014, provisional application No. 62/072,568, (Continued)

(51) Int. Cl.
*A61B 5/021* (2006.01)
*A61B 8/04* (2006.01)
(Continued)

(52) U.S. Cl.
CPC ........ *A61B 5/02108* (2013.01); *A61B 5/0059* (2013.01); *A61B 5/0082* (2013.01); (Continued)

(58) Field of Classification Search
None
See application file for complete search history.

(56) References Cited

U.S. PATENT DOCUMENTS 5,309,916 A * 5/1994 Hatschek ............... A61B 5/021
600/452
5,406,952 A   4/1995 Barnes et al.
(Continued)

FOREIGN PATENT DOCUMENTS

CN     104138253 A    11/2014
JP     2011239972 A   12/2011
(Continued)

OTHER PUBLICATIONS

Bouwmeester J C., et al., "Partitioning pulmonary vascular resistance using the reservoir-wave model", Journal of Applied Physiology, vol. 115, No. 12, Dec. 15, 2013 (Dec. 15, 2013), pp. 1838-1845, XP055207985, ISSN: 8750-7587, DOI: 10.1152/japplphysiol.00750.2013 pp. 1840, 184.

(Continued)

*Primary Examiner* — Katherine Fernandez
*Assistant Examiner* — Bradley Impink
(74) *Attorney, Agent, or Firm* — The Marbury Law Group/Qualcomm

(57) ABSTRACT

Systems, methods, and devices of the various embodiments enable continuous non-invasive monitoring of blood pressure with a minimum of interference. The various embodiments may provide a method for adaptation for the calibration for continuous measurements of blood pressure, wherein the measured quantity may be related to an arterial lumen or arterial cross sectional area comprising calibrating the conversion for incremental variations of arterial properties and absolute value adaptation by exploitation of the exponential decay during the diastole. In various embodiments, continuous calibration of a non-interfering blood pressure measurement device may be initiated based on a change in mean arterial pressure being greater than a thresh- (Continued)

old value, such as a pressure value associated with an actual measured distension of a patient's artery.

30 Claims, 9 Drawing Sheets

Related U.S. Application Data filed on Oct. 30, 2014, provisional application No. 62/072,601, filed on Oct. 30, 2014.

(51) Int. Cl.
| | | |
|---|---|---|
| *A61B 5/00* | (2006.01) | |
| *A61B 5/053* | (2006.01) | |
| *A61B 5/11* | (2006.01) | |
| *A61B 5/02* | (2006.01) | |
| *A61B 5/107* | (2006.01) | |

(52) U.S. Cl.
CPC .......... *A61B 5/021* (2013.01); *A61B 5/02116* (2013.01); *A61B 5/0535* (2013.01); *A61B 5/1126* (2013.01); *A61B 5/6898* (2013.01); *A61B 5/725* (2013.01); *A61B 5/726* (2013.01); *A61B 5/7275* (2013.01); *A61B 5/7278* (2013.01); *A61B 5/7282* (2013.01); *A61B 5/7285* (2013.01); *A61B 8/04* (2013.01); *A61B 5/02007* (2013.01); *A61B 5/053* (2013.01); *A61B 5/1075* (2013.01); *A61B 2560/0223* (2013.01); *A61B 2560/0238* (2013.01); *A61B 2560/0242* (2013.01); *A61B 2560/0247* (2013.01); *A61B 2562/0214* (2013.01); *A61B 2562/0219* (2013.01)

(56) References Cited

U.S. PATENT DOCUMENTS

| | | | |
|---|---|---|---|
| 6,322,515 B1* | 11/2001 | Goor | A61B 5/02007 |
| | | | 600/481 |
| 7,674,231 B2 | 3/2010 | McCombie et al. | |
| 8,313,439 B2 | 11/2012 | McCombie et al. | |
| 8,585,602 B2 | 11/2013 | Crabtree et al. | |
| 8,672,854 B2 | 3/2014 | McCombie et al. | |
| 8,690,785 B2 | 4/2014 | Lading | |
| 2006/0211942 A1* | 9/2006 | Hoctor | A61B 5/02125 |
| | | | 600/438 |
| 2007/0055163 A1* | 3/2007 | Asada | A61B 5/02225 |
| | | | 600/485 |
| 2007/0167844 A1 | 7/2007 | Asada et al. | |
| 2007/0197921 A1* | 8/2007 | Cohen | A61B 5/02028 |
| | | | 600/485 |
| 2010/0274143 A1 | 10/2010 | Kim et al. | |
| 2011/0009718 A1 | 1/2011 | Gavish | |
| 2011/0208066 A1 | 8/2011 | Gnadinger | |
| 2015/0327784 A1 | 11/2015 | Lading | |
| 2015/0327786 A1 | 11/2015 | Lading | |

FOREIGN PATENT DOCUMENTS

| | | |
|---|---|---|
| JP | 2012061131 A | 3/2012 |
| JP | 2013220243 A | 10/2013 |
| WO | 2005065042 A2 | 7/2005 |
| WO | 2014074901 A1 | 5/2014 |
| WO | 2014195578 A1 | 12/2014 |

OTHER PUBLICATIONS

Wang J J., et al., "Systemic venous circulation. Waves propagating on a windkessel: relation of arterial and venous windkessels to systemic vascular resistance", AJP: Heart and Circulatory Physiology, vol. 290, No. 1, Aug. 12, 2005 (Aug. 12, 2005), pp. H154-H162, XP055207961, ISSN: 0363-6135, DOI: 10.1152/ajpheart. 00494.2005 p. H155.

Eiken O., et al., "Blood Pressure Regulation V: In Vivo Mechanical Properties of Precapillary Vessels as Affected by Long-Term Pressure Loading and Unloading," European Journal of Applied Physiology, 2014, vol. 114 (3), pp. 499-509.

Xuan F.W., "An Exploration on Real-time Cuffless Blood Pressure Estimation for e-Home Healthcare," 2011, 96 pages.

International Search Report and Written Opinion—PCT/US2015/ 031538—ISA/EPO—dated Aug. 27, 2015.

McCombie D B., et al., "Adaptive hydrostatic blood pressure calibration: Development of a wearable, autonomous pulse wave velocity blood pressure monitor", 2007 Annual International Conference of the IEEE Engineering in Medicine and Biology Society: [EMBC '07]; Lyon, France, Aug. 22-26, 2007; [In Conjunction With the Biennial Conference of the Societe Francaise de Genie Biologique et Medical (SFGB, Aug. 22, 2007 (Aug. 22, 2007), pp. 370-373, XP031336180, ISBN: 978-1-4244-0787-3 abstract.

* cited by examiner

CONTINUOUS CALIBRATION OF A BLOOD PRESSURE MEASUREMENT DEVICE

RELATED APPLICATIONS

This application claims the benefit of priority to U.S. Provisional Application No. 62/000,078 entitled "Method of Calibrating a Non-Interfering Continuous Blood Pressure Measurement Device" filed May 19, 2014; U.S. Provisional Application No. 62/072,568 entitled "Continuous Calibration of Non-Interfering Blood Pressure Device" filed Oct. 30, 2014; and U.S. Provisional Application No. 62/072,601 entitled "A Method of Estimating the Transmural Pressure in an Artery of a Subject with a Non-Interfering Continuous Blood Pressure Measuring Device" filed Oct. 30, 2014, the entire contents of each of which are hereby incorporated by reference.

BACKGROUND

Devices for measuring cardiovascular properties suffer from the problem that the measurement itself interferes strongly with the state of the subject, thereby leading to erroneous results. This is especially the case for current cuff-based methods that may impart a significant physiological impact. In current cuff-based methods, the systolic blood pressure is obtained by completely or at least substantially blocking an artery, which in most cases is the brachial artery in the upper arm. Blocking the artery affects pulse pressure propagation and pulse pressure shapes, which may only be tolerated in the peripheral system. Further, the diastolic pressure is derived from measurements obtained when the transmural pressure (pressure difference between the outside and the inside of an artery) is close to zero, which implies those measurements are made under conditions that are far from normal.

It is also well recognized that traditional methods based on inflatable cuffs and measurements performed in a clinical environment may have strong psychological effects causing elevation of blood pressure. The phenomenon is commonly called "white coat syndrome" or "white coat hypertension." So-called "masked hypertension" is a contrasting phenomenon in which blood pressure is elevated during normal daily activities but not in a medical office setting.

Additionally, blood pressure often exhibits considerable variability over time. Thus, identifying diurnal or other temporary variations in blood pressure may be very important for proper diagnosis of hypertension. It has also recently been shown that performing ambulatory blood pressure measurements is overall cost-effective.

It is therefore desirable to provide a device for measuring blood pressure that does not interfere with the normal bodily functions or at least does not perturb an artery being measured and that may measure blood pressure continuously and over a longer period of time.

SUMMARY

The systems, methods, and devices of the various embodiments enable continuous non-invasive monitoring of blood pressure with a minimum of interference. The various embodiments provide methods for measurement calibration in a manner that is suitable for continuous measurements of blood pressure. In such embodiment methods the measured quantity may be related to an arterial lumen or arterial cross sectional area including calibrating the conversion for incremental variations of arterial properties and absolute value adaptation by exploitation of the exponential decay during the diastole. In various embodiments, continuous calibration of a non-interfering blood pressure measurement device may be initiated based on a change in mean arterial pressure being greater than a threshold value, such as a pressure value associated with an actual measured distension of a patient's artery.

BRIEF DESCRIPTION OF THE DRAWINGS

The accompanying drawings, which are incorporated herein and constitute part of this specification, illustrate exemplary embodiments of the claims, and together with the general description given above and the detailed description given below, serve to explain the features of the claims.

DETAILED DESCRIPTION

Figure 1A:
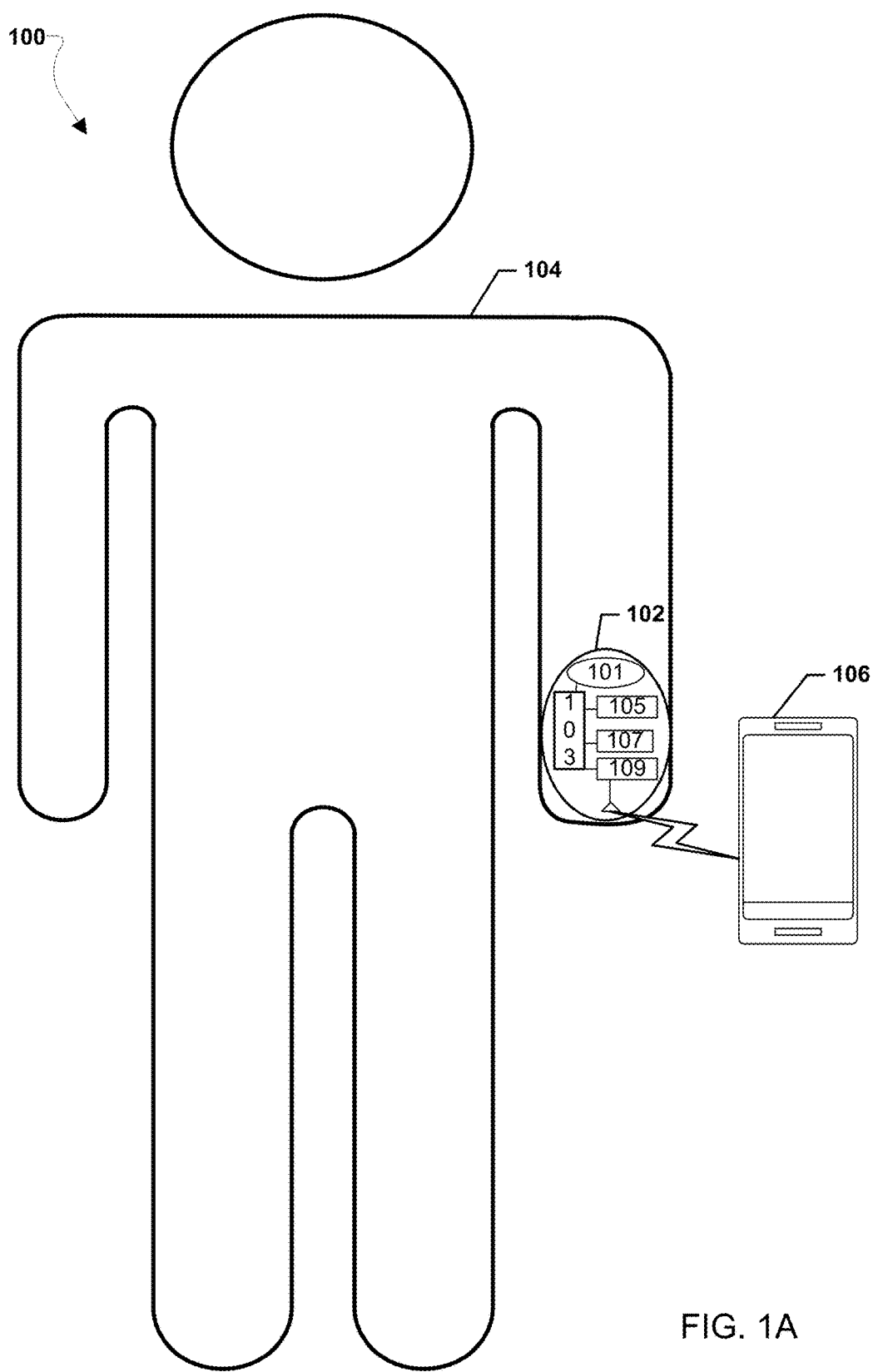
FIG. 1A is a block diagram of an embodiment system including an embodiment blood pressure measuring device placed on a subject.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

The word "exemplary" is used herein to mean "serving as an example, instance, or illustration." Any implementation described herein as "exemplary" is not necessarily to be construed as preferred or advantageous over other implementations.

The terms "computing device" are used herein to refer to any one or all of cellular telephones, smart-phones, web-pads, tablet computers, Internet enabled cellular telephones, Wi-Fi enabled electronic devices, laptop computers, dedicated healthcare electronic devices, personal computers, and similar electronic devices equipped with at least a processor and configured to communicate with an blood pressure measuring device described herein, such as a negligible interfering and negligible perception configuration or form blood pressure measuring device (e.g., a wearable patch, bracelet, anklet, watch, etc.).

The various embodiments provide methods and devices for continuous non-invasive monitoring of blood pressure with a minimum of interference to the measurement. The various embodiments may enable non-interfering measurements of blood pressure.

In various embodiments a blood pressure measuring device may provide an output that varies proportionally with the variations of the cross-sectional area of an artery at a location of the measurement. In some embodiments, the proportionality may be for incremental changes or fluctuations and not for the absolute values because of the bias terms discussed further below. The various embodiments may provide outputs associated with the area or lumen of an artery, and thus to the square of the diameter. Cross-sectional area and lumen (volume) may be proportional because expansion in the direction of the artery may be negligible. The placement of the blood pressure measuring device and/or the location of the measurement may be at any location on a patient, such as a limb (e.g., an arm, a wrist, a finger, etc.).

The various embodiments may measure arterial lumen or cross-sectional area with a bias term. In order to convert such measurements to pressure, the sensitivity of blood pressure measuring device, as well as the arterial stiffness, may be needed and a bias term may be determined. In the various embodiments, variations of the hydrostatic pressure (for example an elevation difference of 60 cm may correspond to a 47 mmHg pressure change, while the Mean Arterial Pressure at heart level may be around 100 mmHg) may be continuously monitored along with outputs from an elevation sensor, such as a 3D accelerometer with measurements integrated in order to detect position changes, a high resolution barometer configured to output the elevation or change in elevation of the measuring location, etc. When the pulse rate is constant, the "driving pulse pressure" may be assumed to be unchanged and the pulse pressure may be assumed to be constant, and thus the only pressure change may be caused by the change of the hydrostatic pressure due to changes in elevation of the measuring location. This presumption that the only cause of the change in pressure is the change of the hydrostatic pressure may enable a method of calibration for incremental changes.

The absolute pressure may be evaluated through analysis of the exponential decay of the diastolic part of the pulse (i.e., the last part of the pulse), which converges towards the vein pressure, generally a few mmHg, a fitting procedure may give the decay constant and the correction to the bias term. Thus, in the various embodiments both pulse pressure and mean arterial pressure may be estimated. Using these estimates, systolic and diastolic pressures may be determined with a temporal resolution unattainable by traditional cuff-based devices and without any interference of the artery on which measurements may be performed. Additionally, the various embodiments may eliminate the need for measuring local Pulse Wave Velocity and arterial diameter to determine blood pressure.

In the various embodiments, variations of the measured quantity may be generally proportional to the variations of the cross-sectional area of the artery, but may include an unknown additive bias term. The proportionality constant and the bias may change, but typically over time scales much longer than the duration of a single pulse. The duration of a single pulse is typically about one second, but the length of a single pulse may vary over time and from individual to individual.

The arterial pressure P and the artery cross-sectional area may be related by a stress-strain relation that generally may be assumed to be exponential. The pressure pulses associated with the beating of the heart may be smaller than the mean pressure and a local linear relation between pressure variations and cross-sectional area variations of the artery can be assumed. The gradient of the relation may define the instantaneous incremental arterial stiffness or elasticity. The stiffness may not be constant, and the stiffness may continuously adapt to the state of the subject (i.e., patient). The response time may typically be in the order of minutes or longer, but may be much shorter in cases of extraordinary changes of the environment to which the subject is exposed. Incremental pressure and lumen changes may be related by the gradient of the stress-strain relation. In general, the lumen and the cross-sectional area of peripheral arteries may be proportional since the variations in the direction of the artery may be negligible: The elastic properties of peripheral arteries may be predominantly given by smooth muscles arranges in a spiral pattern—presumably arranged in such a way that the arterial expansion upon a pressure increase predominantly may be in the radial direction and negligible in the longitudinal direction.

In the various embodiments, the pressure pulse occurring after each contraction of the left heart ventricle can be considered to include three parts. The first part may be the immediate rise of the pressure as a consequence of the ejection from the heart, i.e., the systole phase. The second part may include an exponentially decaying pressure occurring in the diastole phase. The decay may asymptotically approach the venous pressure, which may be only a few mmHg, but may be terminated by the occurrence of the subsequent pulse. The exponential decay may be caused by the arterial system being connected with the veins through capillary network with a high fluid-flow resistivity and the veins being much more elastic than the arteries. Thus, the venous system may essentially behave in a manner that can be represented as a capacitor. Propagation effects may play an insignificant role for the decay since the time constant of the decay may be much larger than the pulse propagation time through the arterial system. The third part may represent reflections from discontinuities in the arterial system such as bifurcations or diameter changes in the arterial system, particularly in the vicinity of a sensor.

In the various embodiments, the pulse rate averaged over time, such as averaged over about one minute of measurements, may play an important role. There may be an inverse relationship between heart rate and central blood pressure, but often a positive correlation is encountered between heart rate and peripheral blood pressure. It may be assumed that if the heart rate is constant—except for the very short term heart rate variability—then the pulse pressure may also be constant and the only change in the measured blood pressure may be caused by a change of the hydrostatic pressure. The hydrostatic pressure affecting the blood pressure in an artery may be exclusively given by the elevation of an arterial segment relative to a reference point if it is assumed that the fluid in the system is incompressible, i.e. its density is constant, and that the gravitation acceleration is constant. The change in hydrostatic pressure $P_{hs}$ encountered by moving a measuring location from one position to another position separated by a distance h in the direction of gravity (i.e., height) may simply be given by: $P_{hs}=\rho g h$, where $\rho$ is the density of the fluid and g is the gravitational acceleration.

For example, the difference in hydrostatic pressure at the wrist of an arm of length 60 cm raised to a straight upward position and a horizontal position, respectively, may be 47.4 mmHg, which may be significant relative to the mean arterial pressure at the elevation of the heart (typically around 100 mmHg). The siphon effect may be neglected if the fluid system is terminated into a very high fluid impedance unit, which is the case for most of the arterial systems in which the high resistance capillary network provides the connection from arteries to veins.

The systems, methods, and devices of the various embodiments may enable continuous estimation of blood pressure based on measured electrical impedance (or admittance, i.e., the inverse of impedance) as a function of time. The various embodiments may continuously estimate blood pressure based on measured electrical impedance as a function of time by continuously adapting to changes of the arterial properties of a patient (i.e., subject) in such a way that no special action may be required by the patient and no sensation may be felt by the patient.

In various embodiments, a blood pressure measuring device may initially be calibrated for the correct arterial properties when a measuring session is started. In various embodiments, a blood pressure measuring device may initially be calibrated in any manner that may enable the blood pressure measuring device to be set for the correct arterial properties for a patient at an initial time. For example, a blood pressure measuring device may be calibrated to measure a quantity (X) monotonically related to the cross sectional area (A) of an artery arranged in the vicinity of a sensor of the blood pressure measuring device by: providing a first model that describes the relationship between the output (X) of the sensor and the cross sectional area (A) of the artery and representing the first model with a first equation (A=f(X)) having a first number of unknown parameters; providing a second model that describes the relationship between the cross sectional area (A) of an artery and the transmural pressure (P) in the artery and representing the second model with a second equation (P=g(A)) having a second number of unknown parameters; substituting the first equation (f) into the second equation (g) to get a third equation, P=c(X), representing the relationship between the output of the sensor and the transmural pressure in the artery, the third equation (c) having a number (z) of unknown parameters; attaching the blood pressure measuring device to a limb of a subject such that the sensor is arranged in the vicinity of an artery in the limb of the subject; placing the limb of the subject into z positions so that the measurement location of the sensor arrives at z different heights with regard to a reference height; at each of the z different heights, measuring and recording the average value of the output of the sensor together with the height of the measurement location of the sensor relative to the reference height; and using the known effect of the hydrostatic force on the transmural pressure at the different heights of the measurement location of the sensor to find the unknown parameters of the third equation (c).

In the various embodiments, when a change $\Delta X$ of the measured quantity X is observed jointly with a possible change of elevation of the measuring site, the expected change in blood pressure, caused by the change of hydrostatic pressure, may be evaluated. Further, if the change $\Delta X$ and possible change of elevation of the measuring site occur during a time interval in which the pulse rate is constant, then the only cause of change in blood pressure at the measuring site is the change in hydrostatic pressure. This may provide for an estimate of the current relation between incremental pressure change $\Delta P$ and incremental change of measured quantity $\Delta X$, i.e. for determining k in the equation $$\Delta P = k \times \Delta X. \tag{1}$$

Knowing the incremental sensitivity, the pulse pressure may be determined based on an exponential stress-strain function and the incremental variation between the two observation times using Eq. (1). The absolute pressure may be obtained by fitting the diastole to the exponential decay function. The fitted exponentially decaying function may asymptotically approach the pressure in the veins. However, the bias of the measured quantity converted to pressure will in general be much larger than the venous pressure. Knowing the asymptotic value of the decay may facilitate an estimate of the absolute pressure. For example, knowing that the asymptotic value should be approximately the vein pressure estimated to within 0-5 mmHg may provide an estimate of the absolute pressure value with an uncertainty equal to the uncertainty of the vein pressure, such as 0-5 mmHg. A complete stress-strain relationship may also be determined by recording a measured quantity at a sequence of different elevations for which the hydrostatic pressure may be evaluated and fit to the exponential relationship of the data.

In the various embodiments, a sensor, such as an arterial measurement sensor, may provide an output, X, that is proportional to the instantaneous arterial cross-sectional area, but that may also include an unknown additive bias term. The variations of the sensor output may provide the equivalent variations of the arterial cross-section. One problem to be solved is to convert the sensor output to properly calibrated blood pressure. The conversion is in general not static because of the varying arterial stiffness. The measuring bias may change as a consequence of movements of the limb on which the measurement is performed, which may correspond to elevation changes at the measurement site. Bias changes may not occur immediately with elevation changes. Rather, in various embodiments bias changes may be assumed to be relatively slow, e.g., on time scales of at least several minutes which may be caused by relatively slow variations of the properties of the veins of a subject. The incremental conversion from sensor signal to lumen may also change as a consequence of changing posture/ position of the patient.

In the various embodiments, an elevation sensor may provide an output that may be continuously converted to a measure of the elevation of the measuring location. For example, the elevation sensor may be a 3D inertial sensor such as an accelerometer, where elevation changes may be inferred from integration of the accelerometer output. As other examples, the elevation sensor may be a barometer, magnetic near-field device, or any other type sensor configured to measure of the elevation or changes in elevation of the measuring location.

Individual pulses may exhibit considerable variability both in amplitude, pulse shape and in pulse length. In order to obtain a characteristic pulse, conditional averaging may be applied in various embodiments. A conditional average may be obtained by averaging a set of numbers in which a given condition has to be fulfilled for each of the numbers. In an embodiment, it may be the amplitudes $X(t_{i,j})$ where the first index i represents a fixed time from a reference time of the pulse. The reference time may be defined by the time in which the largest positive slope of the pulse is observed. For example, the reference time may be at the first zero-crossing of the high-pass filtered pulse. If a number of pulses are recorded then the second index j may be the pulse number. In an embodiment, each of the i values of a pulse may be averaged over all pulses, that is over j. The result may be a pulse representing the average pulse averaged over all the recorded pulses.

In an embodiment, a method for measuring blood pressure may include selecting a location on the body for the measurement, such as a wrist, a finger, or some other location where arteries are identified. The selected location may be fitted with a blood pressure measuring device including an arterial measurement sensor, such as a non-interfering sensing device, which may measure a quantity proportional to the distension of the artery right below the sensor and an elevation sensor, such as a 3D inertial sensor, which may be supported by a tilt sensor. In an embodiment, the outputs of the sensor (e.g., the arterial measurement sensor), and the elevation sensor may be recorded continuously. The pulse rate may be measured and averaged continuously over a sliding window of a width of from 0.5 minute to about 2 minutes. The elevation may be continuously evaluated and averaged over a few seconds.

In an embodiment, sequences with a constant pulse rate may be selected. The mean of the sensor output may be evaluated for these sequences. The incremental sensitivity (or variation) may then be found to be $k=\Delta P_{hs}/\Delta X$ where $\Delta P_{hs}$ is the change in hydrostatic pressure from one observation time to another observation time and $\Delta X$ is the change of the mean output of the arterial measurement sensor between the two observation times.

In an embodiment, the diastolic parts of measured pulses recorded between the two observation times may be fitted to an exponentially decaying function including an additive bias, i.e. to $$a\exp\left(-\frac{t}{t_0}\right)+b \quad (2)$$

The parameter a is defined by the distension amplitude of the diastolic part of the pulse and b is the bias term caused by the possible contributions from tissues other than the artery and by a possible off-set of the measuring electronics. Time is denoted t and the time-constant of the decay is denoted $t_0$ which is given by the resistance of the capillary network connecting artery with veins in conjunction with the capacity of the arteries.

In an embodiment, diastolic parts may be fitted to the exponentially decaying function on each individual pulse and the fitting parameters may then be averaged over a series of pulses, such as 60 pulses or any other number of pulses. Alternatively the fitting may be performed on pulses obtained by conditional averaging over a series of pulses, such as up to 60 pulses. The diastole may be defined as starting at the time instance after the first dip of the pulse in which the second derivative of the measured pulse waveform with respect to time is positive and ending at the onset of the subsequent pulse (see FIG. 5 below).

In an embodiment, the parameters a and b may be converted to pressure parameters by multiplication with k. In an embodiment, the diastolic blood pressure (DBP) may be estimated by evaluation of the first part of Eq. (2) at the end of the diastole (see FIGS. 3 and 5), multiplying with k and adding the vein pressure, which may be assumed to be 4 mmHg with an uncertainty of 2 mmHg. The diastolic blood pressure estimate may be performed on the individual pulses and averaging the values of a number of pulses. The number of pulses may be from one to 60 or more. Generally 60 pulses may be used since short term fluctuations may be minimized and arterial properties may be generally constant over a period of 60 pulses. The diastolic blood pressure estimate may also be obtained from the pulse obtained by conditional averaging. In a similar manner, the pulse pressure (PP) may be simply obtained from Eq. (1) with averaging as described above.

In an embodiment, the systolic blood pressure (SBP) may be given by $$SBP=DB+PP. \quad (3)$$

In an embodiment, the Mean Arterial Pressure (MAP) may be obtained by finding the mean of the pulse pressures from the start of the systole to the end of the diastole, scaled with k, and with the bias term determined above. Alternatively, the often used approximation $$MAP=\frac{2}{3}DBP+\frac{1}{3}SBP \quad (4)$$

may be applied.

In an embodiment, parameters characterizing the relation of pressure to measured signal as defined by Eq. (1) may be determined based on the mean measured signal as recorded at several elevations. The mean measured signal may be a representation of the average signal over a time that may be at least equal to the length of one pulse. A longer time, such as the average signal over a time equal to at least one respiration period, may eliminate the modulation of the blood pressure that is generally caused by respiration. An upper limit for the averaging time may be the time within which the pulse pressure stays constant or the pulse pressure becomes distributed by movement artifacts. This time can be inferred from the variability of the pulse rate. In an embodiment, sets of data representing the hydrostatic pressure relative to the heart level and the sensor averaged output may be recorded for several different elevations, providing a data set $\{Ph_i, X_i\}$, where the index i indicates the specific elevation. The parameters that define Eq. (1) may then be obtained by fitting the expression to the data noting that $P=Ph+P_{heart}$ with $P_{heart}$ being the MAP at an elevation identical to the elevation of the heart. The MAP may then be defined as $P_{heart}$ and the pulse pressure, PP, may be determined by measuring the dynamic part $\Delta X$ of the measured quantity X, which may be converted to pressure through Eq. 1.

Continuous measurement instructions to the subject may only be feasible at the initialization of a measuring session, as measuring sessions may last 24 hours or longer. Updating the calibration may be needed in the course of a measuring session, which may be achieved by measuring the distension signal, the pulse rate, and the elevation of the measuring location continuously. In response to determining that the elevation changes with a constant pulse rate and the accordingly calculated change of pressure deviates from a threshold value, such as a pressure value associated with the actual measured distension, an update calibration condition may be determined and the device may enter a calibration mode.

In an embodiment, a sensor exploiting bioimpedance variations and preferably with a tetrapolar configuration and an electrode configuration as disclosed in WO2012110042A1 may be utilized to determine blood pressure. In another embodiment, electrodes may be applied to a patient placed in a line right on top of the radial artery and aligned with the direction of the selected artery. At the wrist this may be the radial artery or the ulnar artery. A first set of two electrodes may be placed with a separation somewhat larger than the depth at which the artery is embedded in the limb. At the wrist this may be about 1 cm, but the separation may be considerably larger only confined by the length of the limb. A second set of two electrodes may be placed with a closer separation than in the first set and between the electrodes of the first set. The separation of the electrodes of the second set may be at a minimum given by the depth at which the artery is located but preferably larger. At the wrist this may be a separation of from 5 mm to several centimeters. The sizes of the electrodes may be smaller than the separations, such as 1 mm, 2 mm, or larger. A current oscillating at a frequency, which may be in the range of 10 kHz to 100 MHz, may be injected into the limb. The magnitude of the current may be in the range of 0.1 µA to 2 mA. The field lines associated with the current may be essentially perpendicular close to the skin, because the skin and the subcutaneous fat may have low conductivities. In the artery the electric field lines may become aligned with the direction of the blood filled artery because blood has a relatively high conductivity.

FIG. 1A illustrates an embodiment system 100 including an embodiment blood pressure measuring device 102 placed on a subject 104. In an embodiment, the blood pressure measuring device 102 may include a processor 103 connected to one or more arterial measurement sensors 101, one or more elevation sensor 105, a power source 107, and a radio module 109 connected to an antenna. The one or more arterial measurement sensors 101 may be any type sensor or combination of sensors that may measure arterial properties of the patient 104, either directly or indirectly. As an example, the one or more arterial measurement sensors 101 may be electrical tissue and blood impedance measurement sensors that inject an AC current by one set of electrodes and detect the voltage with another set of electrodes to measure bioimpedance. As another example, the one or more arterial measurement sensors 101 may be optical sensors, such as photoplethysmographic sensors including pulse oximeters. As a further example, the one or more arterial measurement sensors 101 may be ultrasound sensors. As yet another example, the one or more arterial measurement sensors 101 may be surface pressure sensors. As a still further example, the one or more arterial measurement sensors 101 may be impedance sensors, such as impedance plethysmography sensors. The one or more arterial measurement sensors 101 may output measurements of arterial properties to the processor 103 of the blood pressure measurement device 102. The one or more elevation sensors 105 may be any type sensor or combination of sensors that may measure the elevation of the blood pressure measuring device 102 and the limb or other location of the subject 104 to which the blood pressure measuring device 102 may be attached. As examples, the one or more elevation sensors may be three dimensional inertial sensors (e.g., accelerometers, etc.), GPS sensors, etc. The one or more elevation sensors 105 may output elevation measurements to the processor 103 of the blood pressure measurement device 102.

In an embodiment, via the radio module 109 and antenna, the processor 103 of the blood pressure measuring device 102 may establish a wireless connection with a computing device 106, such as a smart phone. In this manner, via the wireless connection with the computing device 106, the processor 103 of the blood pressure measuring device 102 may exchange data with the computing device 106.

In the various embodiments, the blood pressure measuring device 102 may be of any type configuration or form. In an embodiment, the blood pressure measuring device 102 may be a negligible interfering and negligible perception configuration or form device, such as a wearable patch, bracelet, anklet, watch, etc.

Figure 1B:
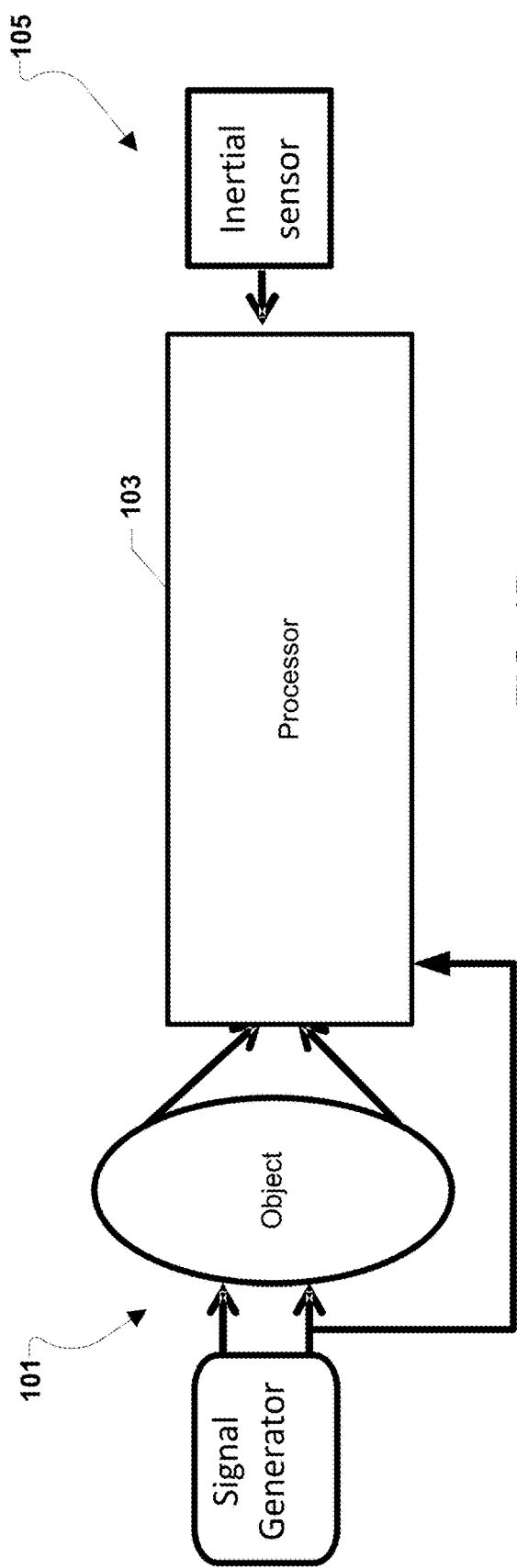
FIG. 1B is a component block diagram of an embodiment blood pressure measuring device.

FIG. 1B is a component block diagram of an embodiment blood pressure measuring device, such as blood pressure measuring device 102 described above with reference to FIG. 1A, illustrating various processing modules of the processor 103. In an embodiment, the blood pressure measuring device illustrated in FIG. 1B may measure blood pressure based on bioimpedances. The arterial measurement sensor 101 may include a signal generator, such as an oscillator, configured to apply an excitation signal, such as an oscillating current, sinusoidal current, etc., via excitation electrodes to an object, such as an artery, and detection electrodes to measure the resulting voltage and provide the voltage to the processor 103. The elevation sensor 105 may comprise an inertial sensor that may be configured to output acceleration measurements to the processor 103.

In an embodiment, the processor 103 of the blood pressure measuring device illustrated in FIG. 1B may measure bioimpedances by controlling the arterial measurement sensor 101 to apply an oscillating current to the excitation electrodes. Outputs from the processor may be pulses and MAP in units of mmHg or in some other selected pressure unit. For example, the pulses and MAP may be transmitted from the processor 103 via a radio module to a computing device, such as a smartphone, for further processing and/or display.

Figure 2:
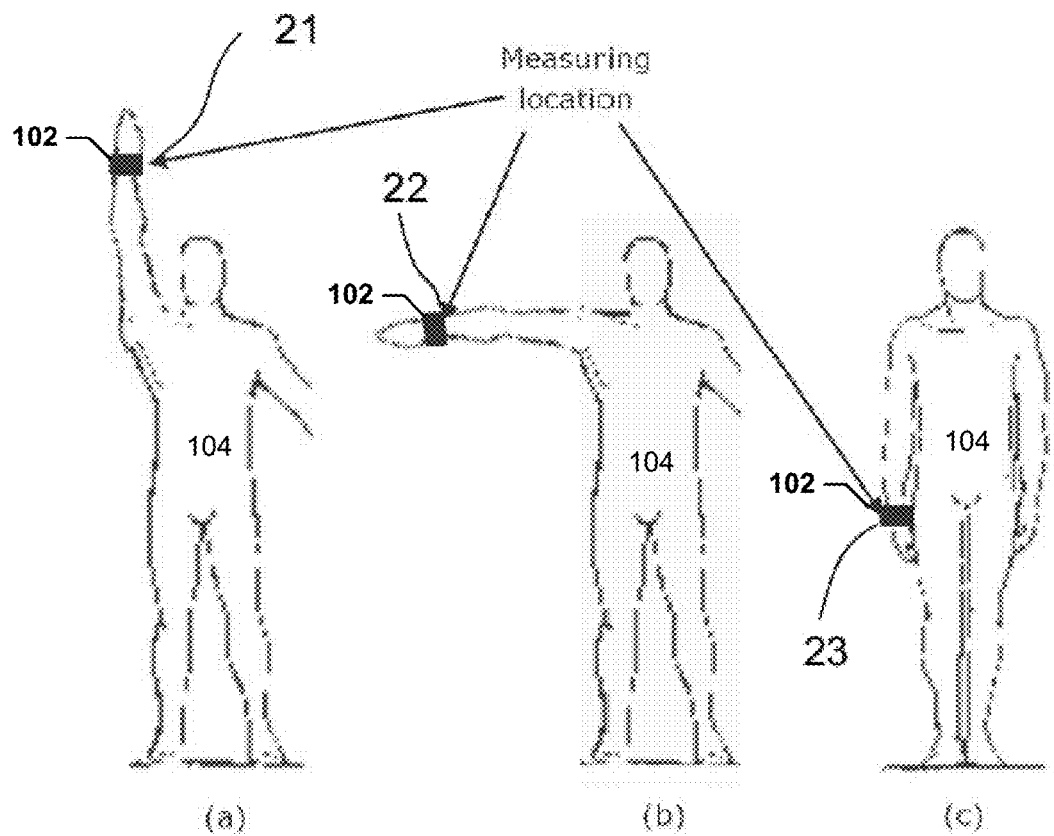
FIG. 2 is a block diagram illustrating movement of a subject's limb and an embodiment blood pressure measuring device.

In an embodiment, the data from the inertial sensor may be supported by signals from a level detector in such a way that the first and last positions require a vertical orientation of the arm (limb), and the measurement between requires a horizontal orientation. FIG. 2 illustrates movement of a subject's limb and an embodiment blood pressure measuring device 102 moving from a first elevation in an upward vertical orientation (21) to a second elevation in a horizontal orientation (22), to a third elevation in a straight downward vertical orientation (23).

Figure 3A:
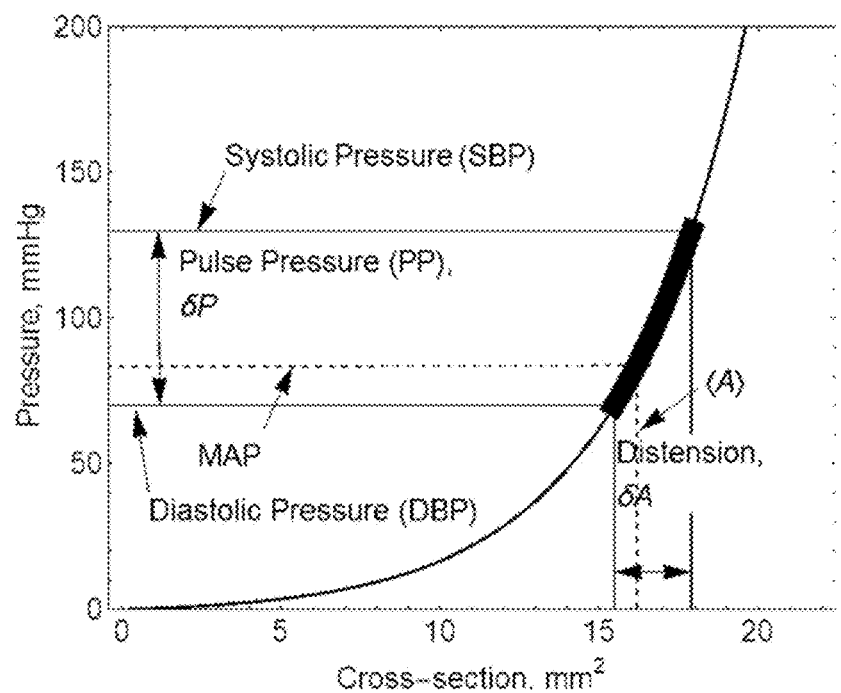
FIG. 3A is a graph of a stress-strain relationship for an artery.
Figure 3B:
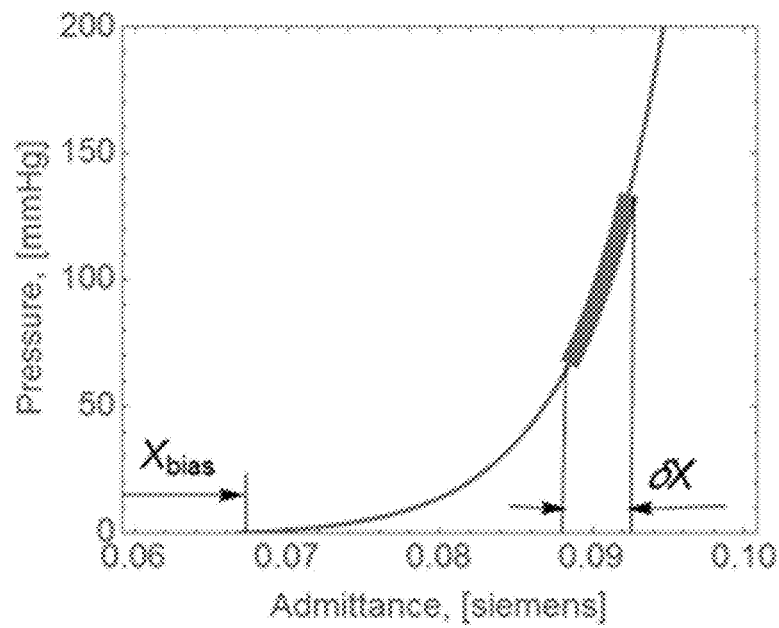
FIG. 3B is a graph of a stress-strain relationship for an artery and illustrates transmural pressure P versus a measured quantity X, respectively.

FIG. 3A is a graph of a stress-strain relationship for an artery. FIG. 3A defines the quantities that may be inferred by the various embodiments, including Systolic Blood Pressure (SBP), Pulse Pressure (PP), δP, MAP, Diastolic Blood Pressure (DBP), Distension, δA, and <A>. FIG. 3B is a graph of a stress-strain relationship for an artery and illustrates transmural pressure P versus a measured quantity X respectively.

Figure 4:
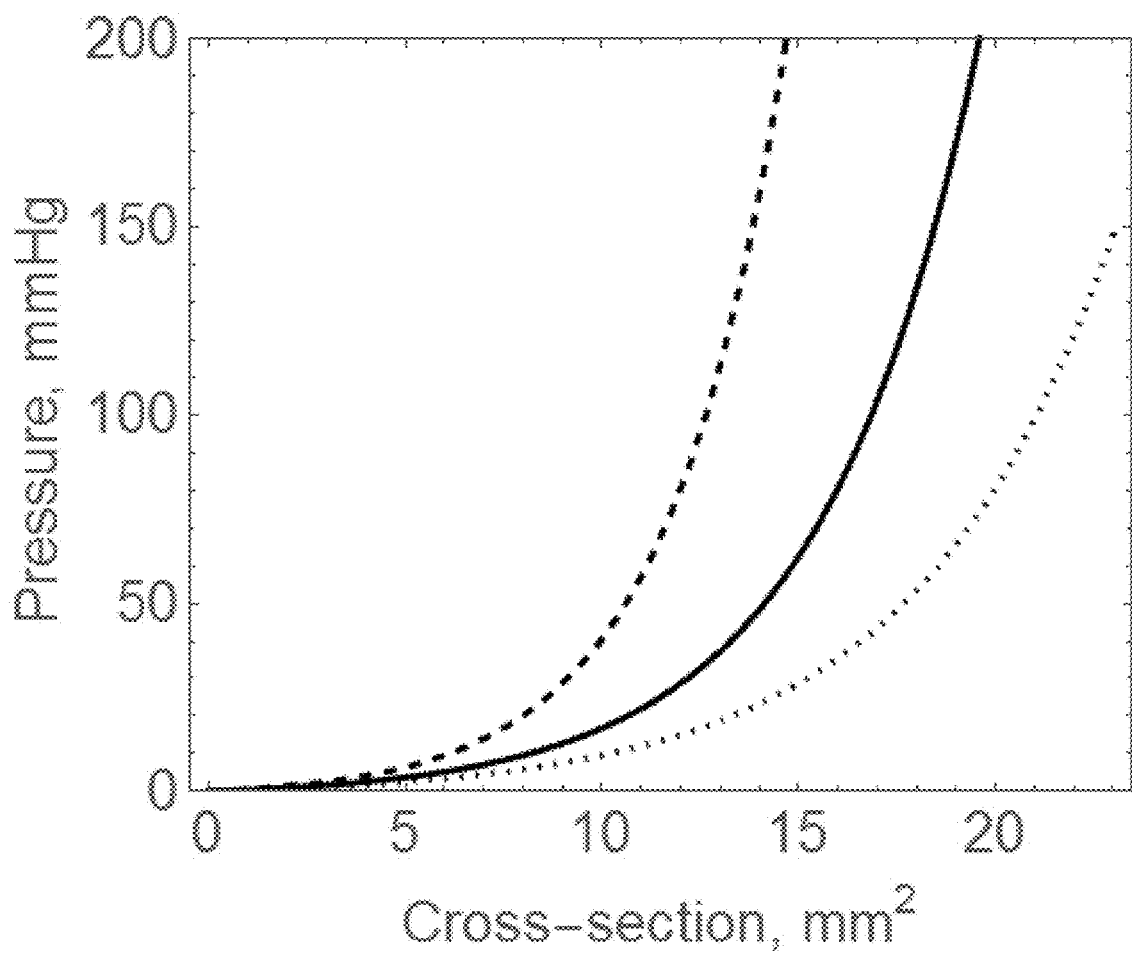
FIG. 4 is a graph of changes in a stress-strain relationship of an artery with tightening or relaxation of the smooth muscles in the artery wall.

FIG. 4 is a graph of changes in a stress-strain relationship of an artery with tightening or relaxation of the smooth muscles in the artery wall. FIG. 4 illustrates how the stress-strain relation may change with changing tightness of the smooth muscles.

Figure 5:
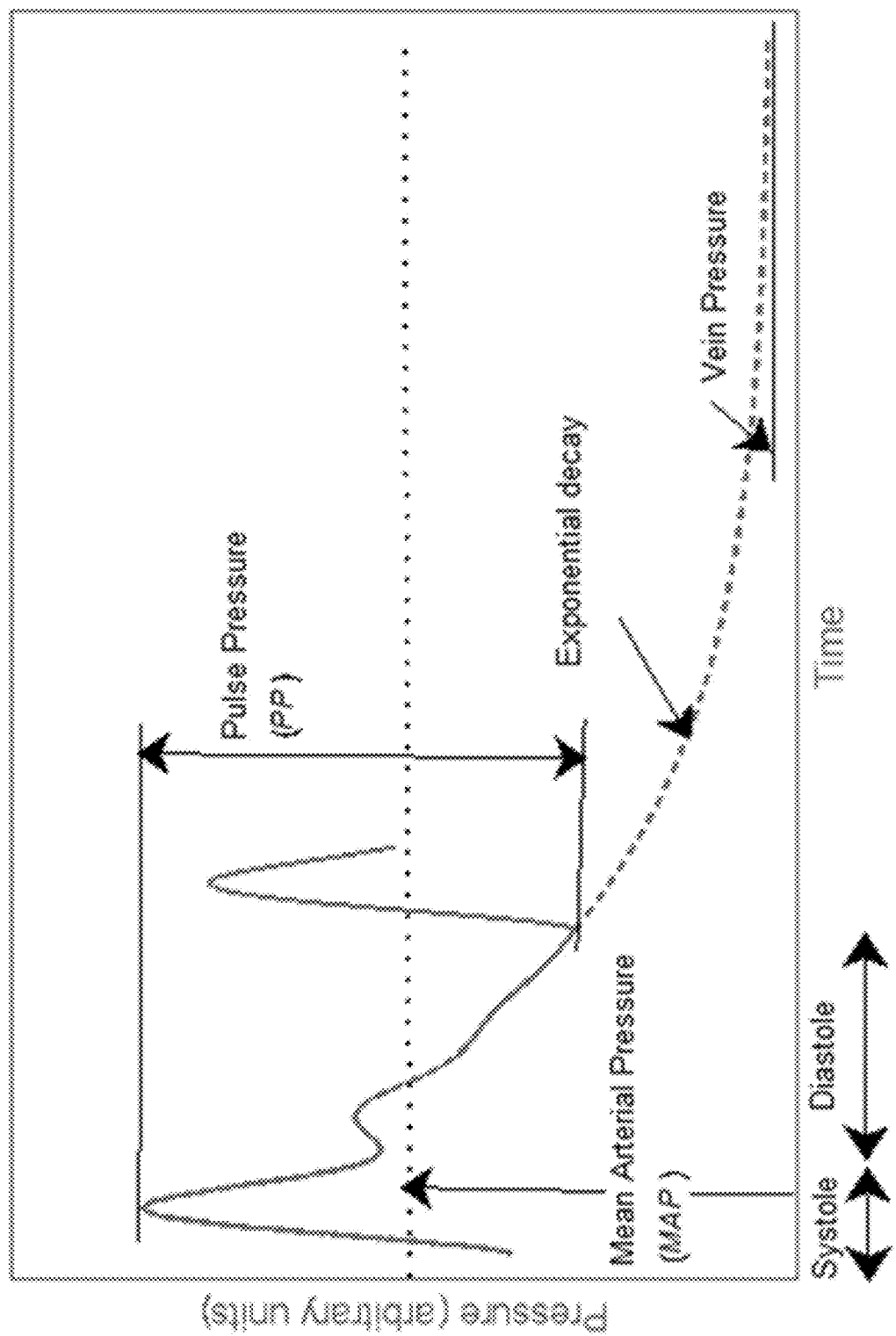
FIG. 5 is a graph of pressure versus time for a single pressure pulse.

FIG. 5 is a graph of pressure versus time for a pressure pulse. FIG. 5 illustrates a typical pressure pulse with the onset in the systolic phase and the exponential decay in the last part of the diastolic phase until the next pulse occurs. A measured impedance variation may, in general, have a large bias. In FIG. 5 the signal was high-pass filtered, which may remove the baseline. While the bias may be eliminated by high-pass filtering, but this may not provide the correct asymptotic value for the decay.

Figure 6A:
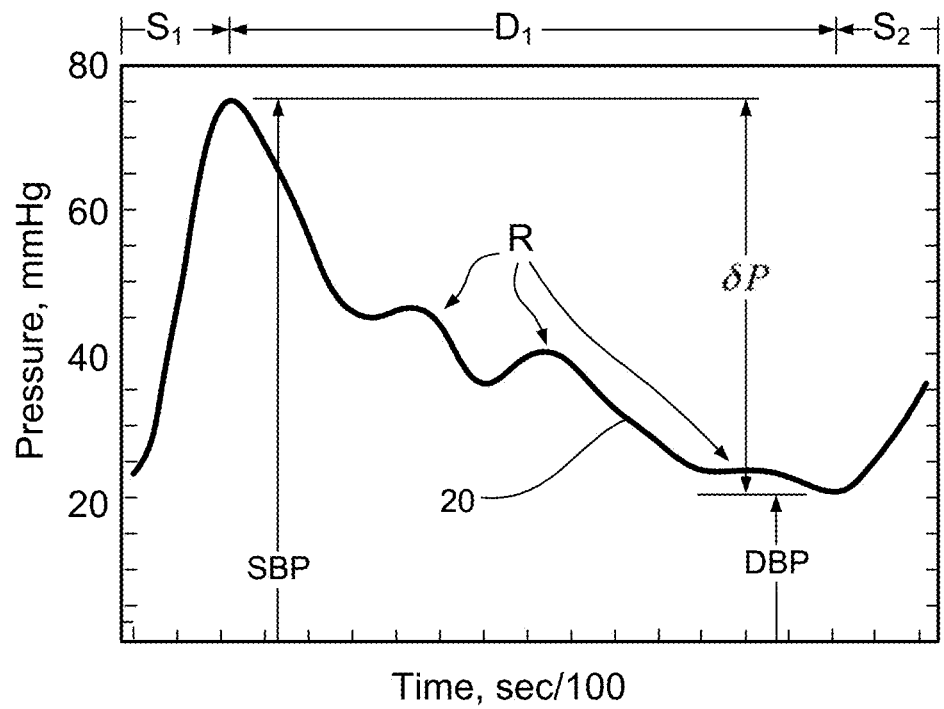
FIG. 6A is a graph of pressure versus time for a pulse pressure of an initial pulse and the start of a subsequent pulse noting particular elements.

FIG. 6A is a graph of a pulse pressure 20 showing the changes in pressure (i.e., the vertical axis, measured in mmHg) over time (i.e., the horizontal axis, measured in sec/100). Pressure pulses occur after each contraction of the left heart ventricle and are considered as having three parts.

A first part $S_1$, referred to as the systolic phase, reflects the immediate rise of the pressure as a consequence of the ejection from the heart.

The second part $D_1$, referred to as the diastolic phase, reflects the fall of the pressure after the systolic phase. The diastolic phase is generally characterized by an exponentially decaying pressure. The exponential decay asymptotically approaches the venous pressure, but is redirected before doing so upon the occurrence of the subsequent pulse, which starts the next pulse's systolic phase $S_2$. The exponential decay may be caused by the arterial system being connected with the veins through capillary network with a high fluid-flow resistivity and the veins being much more elastic than the arteries. Thus, the venous system may essentially behave like a capacitor. Propagation effects may play an insignificant role for the decay since a time-constant of the decay may be much larger than the pulse propagation time through the arterial system.

The pulse pressure 20 also includes reflections R, considered the third part, that result from discontinuities in the arterial system, such as bifurcations or diameter changes, particularly near a sensor.

Figure 6B:
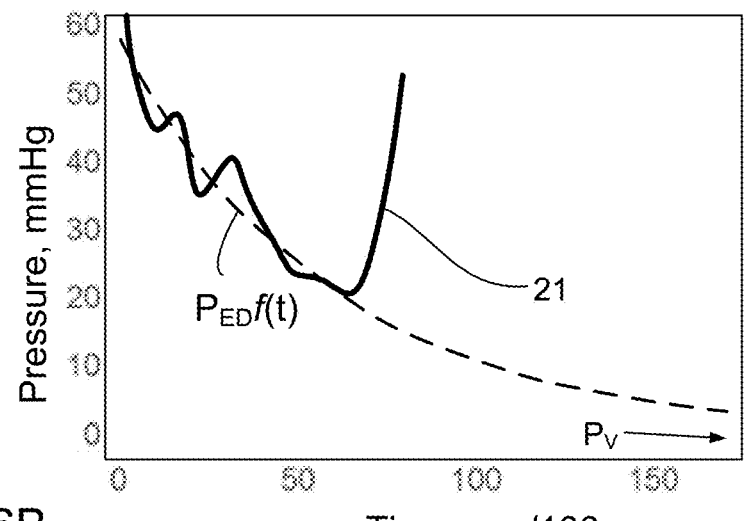
FIG. 6B is a graph of pressure versus time for a pulse pressure of a diastolic phase of an initial pulse and the start of a subsequent pulse, along with a curve matching an exponential decay of the diastolic phase according to various embodiments

FIG. 6B is a graph of another pulse pressure 21 showing the changes in pressure (i.e., the vertical axis, measured in mmHg) over time (i.e., the horizontal axis, measured in sec/100) during a diastolic phase and part of a subsequent systolic phase. Superimposed on the pulse pressure 21 is a decaying exponential function $P_{ED}f(t)$, expressing the exponential decay of the pulse pressure 21 during and extended well beyond the diastolic phase.

Figure 7:
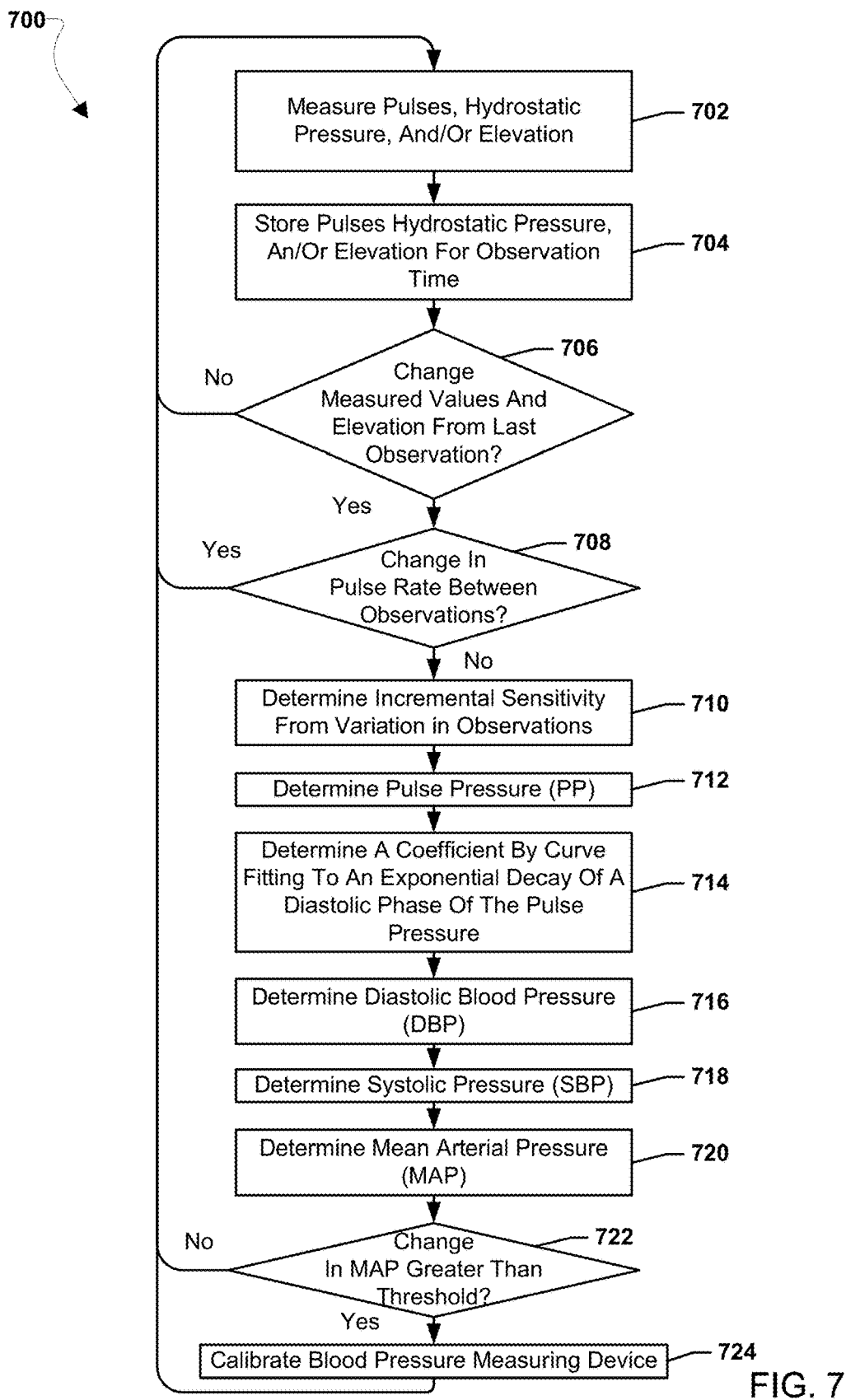
FIG. 7 is a process flow diagram illustrating an embodiment method for continuously estimating blood pressures based on incremental variations of arterial properties.

FIG. 7 illustrates an embodiment method 700 for continuously estimating blood pressures based on incremental variations of arterial properties. In an embodiment, the operations of method 700 may be performed by a processor of a blood pressure measuring device, such as blood pressure measuring device 102 described above. In another embodiment, the operations of the method 700 may be performed by a processor of a computing device, such as a computing device 106 described above, in communication with a blood pressure measuring device, such as blood pressure measuring device 102 described above. In an embodiment, the operations of method 700 may be performed by a processor after an initial calibration procedure to set the correct arterial properties for the blood pressure measuring device when a measuring session is started.

In block 702 the processor may measure pulses, estimate hydrostatic pressure, and elevation at a location of measurement on the body of a patient, such as wrist, finger, or some other location where arteries are identified. In various embodiments, the processor may measure pulses, estimate hydrostatic pressure, and elevation based on outputs from one or more sensors, such as an arterial measurement sensor and elevation sensor. In various embodiments, the pulses, hydrostatic pressures, and elevation may be obtained continuously. In various embodiments, elevation may be averaged over a period of a few seconds and the pulses and hydrostatic pressure may be averaged over that same period. In various embodiments, the pulses may continuously be recorded as they occur, and the pulse rate may be measured and averaged over a sliding window, such as a thirty second window to about a two minute window.

In block 704 the processor may store the measured pulses, hydrostatic pressures, and elevations and/or their averaged measurements corresponding to an observation period. For example, the processor may store the measured pulses, hydrostatic pressures, and elevations and/or their averaged measurements in a memory, such as a database of measured pulses, hydrostatic pressures, and elevations and/or their averaged measurements for different observation periods.

In determination block 706 the processor may determine whether a change in measured values of the artery (e.g., measured values associated with a change in distension and/or cross sectional area of the artery) and elevation both occurred from the last observation. In an embodiment, the processor may compare the measured values or average measurements thereof for the most recent observation time to the measured values or average measurements thereof for the previous observation time to determine whether any change has occurred in the measured values and may compare the elevation of the measurement location from the most recent observation time to the elevation of the measurement location from the previous observation time to determine whether any change has occurred in the elevation. For example, when a change in elevation of the measurement location occurs, the distension of an artery measured at the different elevations may be different, and the change in elevation and measured values may both be determined by comparing the most recent observation and previous observation. In response to determining that no change has occurred in either the distension or the elevation (i.e., determination block 706="No"), the processor may continue to measure pulses, hydrostatic pressure, distension of the artery, and elevation in block 702.

In response to determining that a change has occurred in both the distension and the elevation (i.e., determination block 706="Yes"), the processor may determine whether a change in pulse rate between observation times has occurred in determination block 708. A change in elevation of the measurement location and distension without a change in pulse rate may indicate that the only reason for a change in blood pressure is the change in hydrostatic pressure which may provide an estimate of the current relationship between incremental pressure change and incremental change of measured quantities. In response to determining that a change has occurred in pulse rate (i.e., determination block 708="Yes"), the processor may continue to measure pulses, hydrostatic pressure, distension of the artery, and elevation in block 702.

In response to determining that a change has not occurred in pulse rate (i.e., determination block 708="No"), the processor may determine an incremental variation between observations in block 710. In an embodiment, the variation may be found to be $k=\Delta P_{hs}/\Delta X$ where $\Delta P_{hs}$ is the change in hydrostatic pressure from one observation time to another observation time and $\Delta X$ is the change of the mean output of the arterial measurement sensor between the two observation times. As discussed above, the two different observation times are associated with two different elevations of the measurement location. In an embodiment, the processor may determine an incremental variation between observations by performing two calculations and comparing the results. The first calculation may determine the expected pressure change caused by a change in the elevation of the measurement location based on the previous calibration and distension changes, and the second calculation may determine the change in hydrostatic pressure. The processor may compare the expected pressure change caused by the measurement location elevation change based on the previous calibration and distension to the change in hydrostatic pressure changes. In response to determining that the pressure changes are different, the processor may determine a new calibration is needed, and the new calibration may be obtained from the hydrostatic pressure and the change in the measured quantity averaged over at least one pulse. The "baseline" may then be estimated by the processor using exponential fitting.

In block 712 the processor may determine the pulse pressure (PP). In an embodiment, the pulse pressure (PP) may be simply obtained from Eq. (1) with averaging the values of a number of pulses. The number of pulses may be from one to 60 or more. For general use 60 pulses may be used since short term fluctuations may be minimized and arterial properties may be generally constant. In the various embodiments pulse pressure may be determined based at least in part on an exponential stress-strain function and the incremental variation between the two observation times In block 714, the processor may determine a coefficient for adjusting a stress-strain relationship of the measured artery by curve fitting an exponential decay function to estimated pulse pressures, corresponding to the diastolic phase of a pulse, in order to determining a coefficient for the exponential decay function characterizing the observed decay in pressure. For example, the processor may fit the diastolic parts of the measured pulses between the observation times to an exponentially decaying function and determine the pressure parameters. In other words the processor may determine a coefficient fitting select ones of the estimated pulse pressures corresponding to the diastolic phase fitting an exponentially decaying function including an additive bias representing an exponential decay of a part of a diastolic phase to measured pulses between two observation times. In an embodiment, the diastolic parts of measured pulses recorded between the two observation times may be fitted to an exponentially decaying function including an additive bias, such as Eq. (2) described above. In an embodiment, diastolic parts may be fitted to the exponentially decaying function on each individual pulse and the fitting parameters (e.g., coefficients of the exponentially decaying function) may then be averaged over a series of pulses, such as 60 pulses. Alternatively the fitting may be performed on pulses obtained by conditional averaging over a series of pulses, such as up to 60 pulses. The diastole may be defined as starting at the time instance where the second derivative of the measured pulse waveform with respect to time is positive and ending at the onset of the subsequent pulse. In an embodiment, the parameters a and b may be converted to pressure parameters by multiplication with k. In an embodiment, fitting the diastolic parts of measured pulses between the observation times to an exponential function including an additive bias may result in absolute calibration of the blood pressure measuring device.

In block 716 the processor may determine the diastolic blood pressure (DBP). In an embodiment, the parameters a and b of Eq. (2) may be converted to pressure parameters by multiplication with k. In an embodiment, the diastolic blood pressure (DBP) may be estimated by evaluation of the first part of Eq. (2) at the end of the diastole, multiplying with k and adding the vein pressure, which may be assumed to be 4 mmHg with an uncertainty of 2 mmHg. The diastolic blood pressure estimate may be performed on the individual pulses and averaging the values of a number of pulses. The number of pulses may be from one to 60 or more. For general use 60 pulses may be used since short term fluctuations may be minimized and arterial properties may be generally constant. The diastolic blood pressure estimate may also be obtained from the pulse obtained by conditional averaging.

In block 718 the processor may determine systolic blood pressure (SBP). In an embodiment, systolic blood pressure may be determined according to Eq. (3) described above.

In block 720 the processor may determine Mean Arterial Pressure (MAP). In an embodiment, the MAP may be obtained by finding the mean of the pulse pressures from the start of the systole to the end of the diastole, scaled with k, and a corrective bias term determined by fitting to the exponential decay of the diastole. In another embodiment, the approximation described above in Eq. (4) may be used to determine the MAP.

In determination block 722, the processor may determine whether a change in MAP between observations is greater than a threshold. The threshold value may be a predetermined value stored in a memory and may be associated with a varying condition of the subject. For example, the threshold may be a pressure value associated with an actual measured distension. The processor may determine whether the change in MAP is greater than a threshold by subtracting the MAP determined in block 720 from a previously determined MAP and comparing the determined change in MAP to a threshold value associated with the distension of the artery measured in block 702. In response to determining that the change in MAP is at or below the threshold (i.e., determination block 722="No"), the processor may continue to measure pulses, hydrostatic pressure, distension of the artery, and elevation in block 702.

In response to determining that the change in MAP is greater than the threshold (i.e., determination block 722="Yes"), the processor may calibrate the blood pressure measuring device in block 724. For example, the processor may signal or control the blood pressure measuring device to enter a calibration mode. Additionally, in calibrating the blood pressure measuring device, the processor may update calibration values stored in a memory based on the measured change in hydrostatic pressure, or averages of the measured changes in hydrostatic pressure, between observation times. Upon calibrating the blood pressure measuring device the processor may continue to measure pulses, hydrostatic pressure, distension of the artery, and elevation in block 702.

Figure 8:
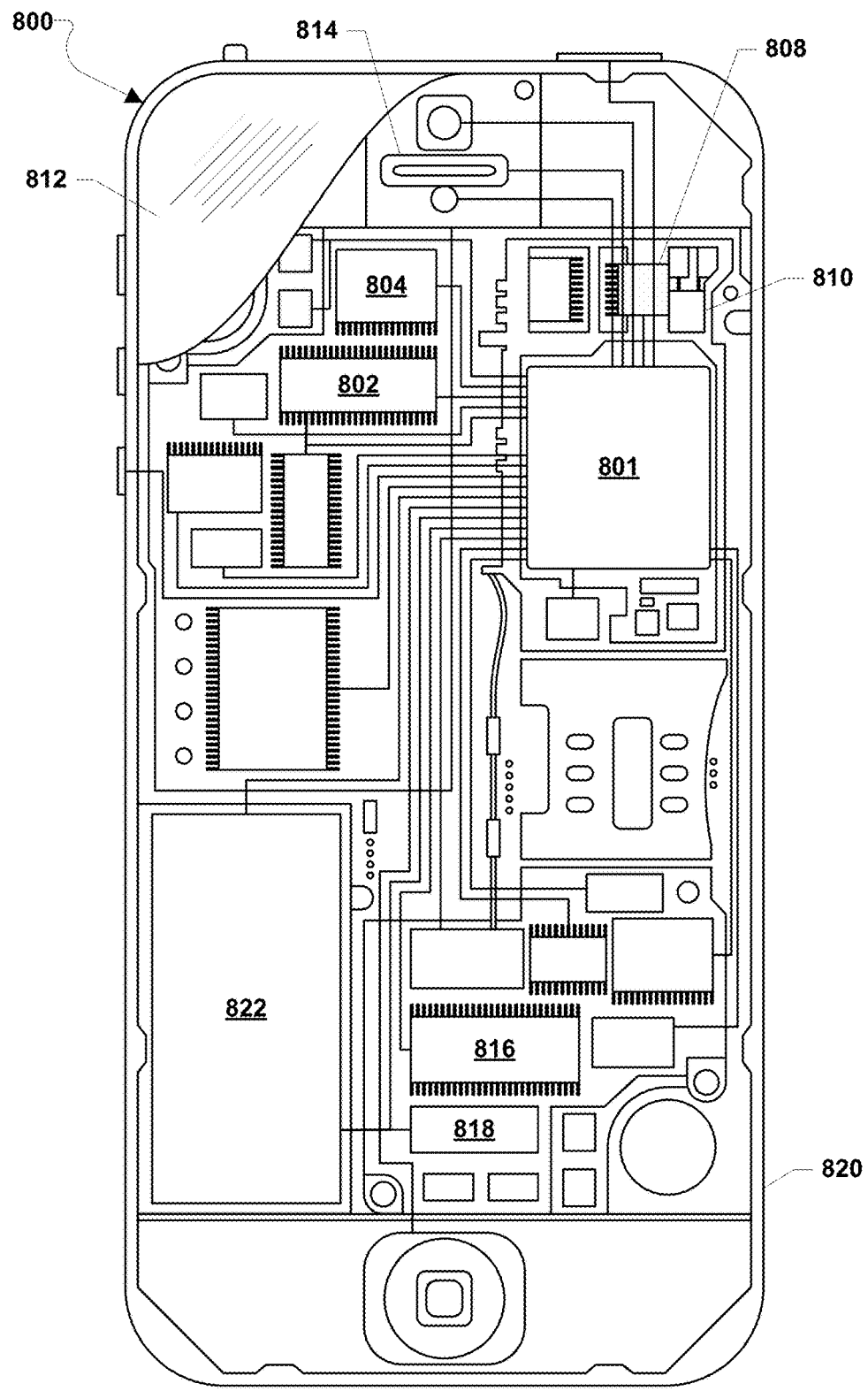
FIG. 8 is a component block diagram of a computing device suitable for use with the various embodiments.

An embodiment blood pressure measuring device may be configured to transmit data to any of a variety of computing devices. For example, FIG. 8 illustrates a computing device 800 suitable for use in various embodiments. The computing device 800 may exchange data to and/or from the blood pressure measuring devices discussed above, such as blood pressure measuring device 102, and may perform one or more of the operations of method 700 described above. For example, DBP, PP, SBP, MAP, and/or measured pulses, hydrostatic pressure, measurements of an artery (e.g., measurements related to distension and/or cross sectional area of an artery), and/or elevation may be sent from the blood pressure measuring device to the computing device 800.

In various embodiments, the computing device 800 may include a processor 801 coupled to a touch screen controller 804 and an internal memory 802. The processor 801 may be one or more multicore ICs designated for general or specific processing tasks. The internal memory 802 may be volatile or non-volatile memory, and may also be secure and/or encrypted memory, or unsecure and/or unencrypted memory, or any combination thereof. The touch screen controller 804 and the processor 801 may also be coupled to a touch screen panel 812, such as a resistive-sensing touch screen, capacitive-sensing touch screen, infrared sensing touch screen, etc. The computing device 800 may have one or more radio signal transceivers 808 (e.g., Peanut®, Bluetooth®, Zigbee®, Wi-Fi, RF, cellular, etc.) and antennae 810, for sending and receiving, coupled to each other and/or to the processor 801. The transceivers 808 and antennae 810 may be used with the above-mentioned circuitry to implement the various wireless transmission protocol stacks and interfaces. The computing device 800 may include a cellular network wireless modem chip 816 that enables communication via a cellular network, such as an eMBMS network, and is coupled to the processor. The computing device 800 may include a peripheral device connection interface 818 coupled to the processor 801. The peripheral device connection interface 818 may be singularly configured to accept one type of connection, or multiply configured to accept various types of physical and communication connections, common or proprietary, such as USB, FireWire, Thunderbolt, or PCIe. The peripheral device connection interface 818 may also be coupled to a similarly configured peripheral device connection port (not shown). The computing device 800 may also include speakers 814 for providing audio outputs. The computing device 800 may also include a housing 820, constructed of a plastic, metal, or a combination of materials, for containing all or some of the components discussed herein. The computing device 800 may include a power source 822 coupled to the processor 801, such as a disposable or rechargeable battery. The rechargeable battery may also be coupled to the peripheral device connection port to receive a charging current from a source external to the computing device 800.

Processors of computing devices suitable for use in various embodiments may be any programmable microprocessor, microcomputer or multiple processor chip or chips that can be configured by software instructions (applications) to perform a variety of functions, including the functions of the various embodiments described above. In the various devices, multiple processors may be provided, such as one processor dedicated to wireless communication functions and one processor dedicated to running other applications. Typically, software applications may be stored in internal memory before they are accessed and loaded into the processors. The processors may include internal memory sufficient to store the application software instructions. In many devices, the internal memory may be a volatile or nonvolatile memory, such as flash memory, or a mixture of both. For the purposes of this description, a general reference to memory refers to memory accessible by the processors including internal memory or removable memory plugged into the various devices and memory within the processors.

Further, those of skill in the art will appreciate that the foregoing method descriptions and the process flow diagrams are provided merely as illustrative examples and are not intended to require or imply that the operations of the various embodiments must be performed in the order presented. As will be appreciated by one of skill in the art the order of operations in the foregoing embodiments may be performed in any order. Words such as "thereafter," "then," "next," etc. are not intended to limit the order of the operations; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope embodiments.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine A processor may also be implemented as a combination of computing devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

The functions in the various embodiments may be implemented in hardware, software, firmware, or any combination thereof. If implemented in software, the functions may be stored as one or more processor executable instructions or code on a non-transitory computer readable medium or non-transitory processor readable medium. The operations of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present invention is not intended to be limited to the embodiments shown herein but is to be accorded the widest scope consistent with the following claims and the principles and novel features disclosed herein.

What is claimed is:

1. A method for calibration of a non-interfering blood pressure measurement device, comprising:
   determining, by a processor, a pulse rate, a distension, a hydrostatic pressure, and an elevation at an artery of a patient at two observation times, wherein the pulse rate, the hydrostatic pressure, and the distension are determined based on a collection of outputs of an arterial measurement sensor of the non-interfering blood pressure measurement device and the elevation is determined based on one or more outputs of an elevation sensor of the non-interfering blood pressure measurement device;
   determining, by the processor, a series of arterial pressures of the artery of the patient between the two observation times based on the collection of outputs of the arterial measurement sensor;
   determining, by the processor, whether a change in both the distension and the elevation occurred between the two observation times;
   determining, by the processor, whether a change in the pulse rate has occurred between the two observation times in response to determining that the change in both the distension and the elevation occurred between the two observation times;
   determining, by the processor, an incremental variation between the two observation times in response to determining that no change in the pulse rate occurred between the two observation times, wherein the incremental variation is a change in hydrostatic pressure between the two observation times over the change in the distension between the two observation times;
   determining, by the processor, an exponentially decaying function representing an exponential decay of the series of arterial pressures in a portion of a diastolic phase of a selected pulse that occurred between the two observation times;
   determining, by the processor, a mean arterial pressure based at least in part on the exponentially decaying function and the incremental variation;
   determining, by the processor, whether a change in mean arterial pressure determined as a difference between the determined mean arterial pressure and a previously determined mean arterial pressure is greater than a threshold pressure; and
   calibrating, by the processor, the non-interfering blood pressure measurement device in response to determining that the change in mean arterial pressure is greater than the threshold pressure, wherein calibrating the non-interfering blood pressure measurement device comprises controlling, by the processor, the non-interfering blood pressure measurement device to enter a calibration mode.

2. The method of claim 1, wherein determining, by the processor, the mean arterial pressure based at least in part on the exponentially decaying function and the incremental variation comprises:
   determining, by the processor, a diastolic pressure based on the exponentially decaying function and the incremental variation;
   determining, by the processor, a systolic blood pressure based at least in part on the determined diastolic pressure; and
   determining, by the processor, the mean arterial pressure as two thirds of the determined diastolic pressure added to one third of the determined systolic blood pressure.

3. The method of claim 1, wherein the arterial measurement sensor is one or more of a bioimpedance sensor, impedance plethysmography sensor, photoplethsmography sensor, ultrasound sensor, and surface pressure sensor.

4. The method of claim 1, wherein calibrating the non-interfering blood pressure measurement device includes updating calibration values stored in a memory of the non-interfering blood pressure measurement device based on the change in mean arterial pressure and the change in distension.

5. The method of claim 1, wherein determining, by the processor, whether the change in the pulse rate has occurred between the two observation times comprises localizing, by the processor, pulses that occurred between the two observation times by one or more of:
   determining a zero crossing of a high-pass filter demodulated signal;
   localizing maximum pulse gradients;
   localizing based on a quantity related to the maximum and minimum of each pulse; and
   wavelet filtering to extract shape and time information.

6. A device, comprising:
   a processor in communication with a non-interfering blood pressure measurement device, wherein the processor is configured with processor executable instructions to perform operations to:
   determine a pulse rate, a distension, a hydrostatic pressure, and an elevation at an artery of a patient at two observation times, wherein the pulse rate, the hydrostatic pressure, and the distension are determined based on a collection of outputs of an arterial measurement sensor of the non-interfering blood pressure measurement device and the elevation is determined based on one or more outputs of an elevation sensor of the non-interfering blood pressure measurement device;
   determine a series of arterial pressures of the artery of the patient between the two observation times based on the collection of outputs of the arterial measurement sensor;
   determine whether a change in both the distension and the elevation occurred between the two observation times;
   determine whether a change in the pulse rate has occurred between the two observation times in response to determining that the change in both the distension and the elevation occurred between the two observation times;
   determine an incremental variation between the two observation times in response to determining that no change in the pulse rate occurred between the two observation times, wherein the incremental variation is a change in hydrostatic pressure between the two observation times over the change in the distension between the two observation times;
   determine an exponentially decaying function representing an exponential decay of the series of arterial pressures in a portion of a diastolic phase of a selected pulse that occurred between the two observation times;
   determine a mean arterial pressure based at least in part on the exponentially decaying function and the incremental variation;
   determine whether a change in mean arterial pressure determined as a difference between the determined mean arterial pressure and a previously determined mean arterial pressure is greater than a threshold pressure; and calibrate the non-interfering blood pressure measurement device in response to determining that the change in mean arterial pressure is greater than the threshold pressure, wherein calibrating the non-interfering blood pressure measurement device comprises controlling the non-interfering blood pressure measurement device to enter a calibration mode.

7. The device of claim 6, wherein the processor is configured with processor executable instructions to perform operations to determine the mean arterial pressure based at least in part on the exponentially decaying function and the incremental variation by:

determining a diastolic pressure based on the exponentially decaying function and the incremental variation;

determining a systolic blood pressure based at least in part on the determined diastolic pressure; and determining the mean arterial pressure as two thirds of the determined diastolic pressure added to one third of the determined systolic blood pressure.

8. The device of claim 6, wherein the arterial measurement sensor is one or more of a bioimpedance sensor, impedance plethysmography sensor, photoplethsmography sensor, ultrasound sensor, and surface pressure sensor.

9. The device of claim 6, wherein the processor is further configured with processor executable instructions to perform operations to calibrate the non-interfering blood pressure measurement device by updating calibration values stored in a memory of the non-interfering blood pressure measurement device based on the change in mean arterial pressure and the change in distension.

10. The device of claim 6, wherein the processor is configured with processor executable instructions to perform operations to determine whether the change in the pulse rate has occurred between the two observation times by localizing pulses that occurred between the two observation times by one or more of:

determining a zero crossing of a high-pass filter demodulated signal;

localizing maximum pulse gradients;

localizing based on a quantity related to the maximum and minimum of each pulse; and wavelet filtering to extract shape and time information.

11. A non-interfering blood pressure measurement device, comprising:

an arterial measurement sensor;

an elevation sensor; and a processor connected to the arterial measurement sensor and elevation sensor, wherein the processor is configured with processor executable instructions to perform operations to:

determine a pulse rate, a distension, a hydrostatic pressure, and an elevation at an artery of a patient at two observation times, wherein the pulse rate, the hydrostatic pressure, and the distension are determined based on a collection of outputs of the arterial measurement sensor and the elevation is determined based on one or more outputs of the elevation sensor;

determine a series of arterial pressures of the artery of the patient between the two observation times based on the collection of outputs of the arterial measurement sensor;

determine whether a change in both the distension and the elevation occurred between the two observation times;

determine whether a change in the pulse rate has occurred between the two observation times in response to determining that the change in both the distension and the elevation occurred between the two observation times;

determine an incremental variation between the two observation times in response to determining that no change in the pulse rate occurred between the two observation times, wherein the incremental variation is a change in hydrostatic pressure between the two observation times over the change in the distension between the two observation times;

determine an exponentially decaying function representing an exponential decay of the series of arterial pressures in a portion of a diastolic phase of a selected pulse that occurred between the two observation times;

determine a mean arterial pressure based at least in part on the exponentially decaying function and the incremental variation;

determine whether a change in mean arterial pressure determined as a difference between the determined mean arterial pressure and a previously determined mean arterial pressure is greater than a threshold pressure; and calibrate the non-interfering blood pressure measurement device in response to determining that the change in mean arterial pressure is greater than the threshold pressure, wherein calibrating the non-interfering blood pressure measurement device comprises controlling the non-interfering blood pressure measurement device to enter a calibration mode.

12. The non-interfering blood pressure measurement device of claim 11, wherein the processor is configured with processor executable instructions to perform operations to determine the mean arterial pressure based at least in part on the exponentially decaying function and the incremental variation by:

determining a diastolic pressure based on the exponentially decaying function and the incremental variation;

determining a systolic blood pressure based at least in part on the determined diastolic pressure; and determining the mean arterial pressure as two thirds of the determined diastolic pressure added to one third of the determined systolic blood pressure.

13. The non-interfering blood pressure measurement device of claim 11, wherein the arterial measurement sensor is one or more of a bioimpedance sensor, impedance plethysmography sensor, photoplethsmography sensor, ultrasound sensor, and surface pressure sensor.

14. The non-interfering blood pressure measurement device of claim 11, wherein the processor is further configured with processor executable instructions to perform operations to calibrate the non-interfering blood pressure measurement device by updating calibration values stored in a memory of the non-interfering blood pressure measurement device based on the change in mean arterial pressure and the change in distension.

15. The non-interfering blood pressure measurement device of claim 11, wherein the processor is configured with processor executable instructions to perform operations to determine whether the change in the pulse rate has occurred between the two observation times by localizing pulses that occurred between the two observation times by one or more of:

determining a zero crossing of a high-pass filter demodulated signal;

localizing maximum pulse gradients;
localizing based on a quantity related to the maximum and minimum of each pulse; and
wavelet filtering to extract shape and time information.

16. A device, comprising:
means for determining a pulse rate, a distension, a hydrostatic pressure, and an elevation at an artery of a patient at two observation times, wherein the pulse rate, the hydrostatic pressure, and the distension are determined based on a collection of outputs of an arterial measurement sensor of a non-interfering blood pressure measurement device and the elevation is determined based on one or more outputs of an elevation sensor of the non-interfering blood pressure measurement device;
means for determining, by the processor, a series of arterial pressures of the artery of the patient between the two observation times based on the collection of outputs of the arterial measurement sensor;
means for determining whether a change in both the distension and the elevation occurred between the two observation times;
means for determining whether a change in the pulse rate has occurred between the two observation times in response to determining that the change in both the distension and the elevation occurred between the two observation times;
means for determining an incremental variation between the two observation times in response to determining that no change in the pulse rate occurred between the two observation times, wherein the incremental variation is a change in hydrostatic pressure between the two observation times over the change in the distension between the two observation times;
means for determining an exponentially decaying function representing an exponential decay of the series of arterial pressures in a portion of a diastolic phase of a selected pulse that occurred between the two observation times;
means for determining a mean arterial pressure based at least in part on the exponentially decaying function and the incremental variation;
means for determining whether a change in mean arterial pressure determined as a difference between the determined mean arterial pressure and a previously determined mean arterial pressure is greater than a threshold pressure; and
means for calibrating the non-interfering blood pressure measurement device in response to determining that the change in mean arterial pressure is greater than the threshold pressure, wherein means for calibrating the non-interfering blood pressure measurement device comprises means for controlling the non-interfering blood pressure measurement device to enter a calibration mode.

17. The device of claim 16, wherein means for determining the mean arterial pressure based at least in part on the exponentially decaying function and the incremental variation comprises:
means for determining a diastolic pressure based on the exponentially decaying function and the incremental variation;
means for determining a systolic blood pressure based at least in part on the determined diastolic pressure; and
means for determining the mean arterial pressure as two thirds of the determined diastolic pressure added to one third of the determined systolic blood pressure.

18. The device of claim 16, wherein the arterial measurement sensor is one or more of a bioimpedance sensor, impedance plethysmography sensor, photoplethsmography sensor, ultrasound sensor, and surface pressure sensor.

19. The device of claim 16, wherein means for calibrating the non-interfering blood pressure measurement device further comprises means for updating calibration values stored in a memory of the non-interfering blood pressure measurement device based on the change in mean arterial pressure and the change in distension.

20. The device of claim 16, wherein means for determining whether the change in the pulse rate has occurred between the two observation times comprises means for localizing pulses that occurred between the two observation times by one or more of:
determining a zero crossing of a high-pass filter demodulated signal;
localizing maximum pulse gradients;
localizing based on a quantity related to the maximum and minimum of each pulse; and
wavelet filtering to extract shape and time information.

21. A non-transitory processor readable medium having stored thereon processor executable instructions configured to cause a processor to perform operations comprising:
determining a pulse rate, a distension, a hydrostatic pressure, and an elevation at an artery of a patient at two observation times, wherein the pulse rate, the hydrostatic pressure, and the distension are determined based on a collection of outputs of an arterial measurement sensor of the non-interfering blood pressure measurement device and the elevation is determined based on one or more outputs of an elevation sensor of the non-interfering blood pressure measurement device;
determining a series of arterial pressures of the artery of the patient between the two observation times based on the collection of outputs of the arterial measurement sensor;
determining, whether a change in both the distension and the elevation occurred between the two observation times;
determining whether a change in the pulse rate has occurred between the two observation times in response to determining that the change in both the distension and the elevation occurred between the two observation times;
determining an incremental variation between the two observation times in response to determining that no change in the pulse rate occurred between the two observation times, wherein the incremental variation is a change in hydrostatic pressure between the two observation times over the change in the distension between the two observation times;
determining an exponentially decaying function representing an exponential decay of the series of arterial pressures in a portion of a diastolic phase of a selected pulse that occurred between the two observation times;
determining a mean arterial pressure based at least in part on the exponentially decaying function and the incremental variation;
determining whether a change in mean arterial pressure determined as a difference between the determined mean arterial pressure and a previously determined mean arterial pressure is greater than a threshold pressure; and
means for calibrating the non-interfering blood pressure measurement device in response to determining that the change in mean arterial pressure is greater than the threshold pressure, wherein calibrating the non-interfering blood pressure measurement device comprises controlling the non-interfering blood pressure measurement device to enter a calibration mode.

22. The non-transitory processor readable medium of claim 21, wherein the stored processor readable instructions are configured to cause a processor to perform operations such that determining the mean arterial pressure based at least in part on the exponentially decaying function and the incremental variation comprises:
   determining a diastolic pressure based on the exponentially decaying function and the incremental variation;
   determining a systolic blood pressure based at least in part on the determined diastolic pressure; and
   determining the mean arterial pressure as two thirds of the determined diastolic pressure added to one third of the determined systolic blood pressure.

23. The non-transitory processor readable medium of claim 21, wherein the stored processor readable instructions are configured to cause a processor to perform operations such that the arterial measurement sensor is one or more of a bioimpedance sensor, impedance plethysmography sensor, photoplethsmography sensor, ultrasound sensor, and surface pressure sensor.

24. The non-transitory processor readable medium of claim 21, wherein the stored processor readable instructions are configured to cause a processor to perform operations such that calibrating the non-interfering blood pressure measurement device further comprises updating, by the processor, calibration values stored in a memory of the non-interfering blood pressure measurement device based on the change in mean arterial pressure and the change in distension.

25. The non-transitory processor readable medium of claim 21, wherein the stored processor readable instructions are configured to cause a processor to perform operations such that determining whether the change in the pulse rate has occurred between the two observation times comprises localizing pulses that occurred between the two observation times by one or more of:
   determining a zero crossing of a high-pass filter demodulated signal;
   localizing maximum pulse gradients;
   localizing based on a quantity related to the maximum and minimum of each pulse; and
   wavelet filtering to extract shape and time information.

26. A system, comprising:
   a non-interfering blood pressure measurement device; and
   a computing device, comprising a processor in communication with the non-interfering blood pressure measurement device, wherein the processor is configured with processor executable instructions to perform operations to:
      determine a pulse rate, a distension, a hydrostatic pressure, and an elevation at an artery of a patient at two observation times, wherein the pulse rate, the hydrostatic pressure, and the distension are determined based on a collection of outputs of an arterial measurement sensor of the non-interfering blood pressure measurement device and the elevation is determined based on one or more outputs of an elevation sensor of the non-interfering blood pressure measurement device;
      determine a series of arterial pressures of the artery of the patient between the two observation times based on the collection of outputs of the arterial measurement sensor;
      determine whether a change in both the distension and the elevation occurred between the two observation times;
      determine whether a change in the pulse rate has occurred between the two observation times in response to determining that the change in both the distension and the elevation occurred between the two observation times;
      determine an incremental variation between the two observation times in response to determining that no change in the pulse rate occurred between the two observation times, wherein the incremental variation is a change in hydrostatic pressure between the two observation times over the change in the distension between the two observation times;
      determine an exponentially decaying function representing an exponential decay of the series of arterial pressures in a portion of a diastolic phase of a selected pulse that occurred between the two observation times;
      determine a mean arterial pressure based at least in part on the exponentially decaying function and the incremental variation;
      determine whether a change in mean arterial pressure determined as a difference between the determined mean arterial pressure and a previously determined mean arterial pressure is greater than a threshold pressure; and
      calibrate the non-interfering blood pressure measurement device in response to determining that the change in mean arterial pressure is greater than the threshold pressure, wherein calibrating the non-interfering blood pressure measurement device comprises controlling the non-interfering blood pressure measurement device to enter a calibration mode.

27. The system of claim 26, wherein the processor is configured with processor executable instructions to perform operations to determine the mean arterial pressure based at least in part on the exponentially decaying function and the incremental variation by:
   determining a diastolic pressure based on the exponentially decaying function and the incremental variation;
   determining a systolic blood pressure based at least in part on the determined diastolic pressure; and
   determining the mean arterial pressure as two thirds of the determined diastolic pressure added to one third of the determined systolic blood pressure.

28. The system of claim 26, wherein the arterial measurement sensor is one or more of a bioimpedance sensor, impedance plethysmography sensor, photoplethsmography sensor, ultrasound sensor, and surface pressure sensor.

29. The system of claim 26, wherein the processor is further configured with processor executable instructions to perform operations to calibrate the non-interfering blood pressure measurement device by updating calibration values stored in a memory of the non-interfering blood pressure measurement device based on the change in mean arterial pressure and the change in distension.

30. The system of claim 26, wherein the processor is configured with processor executable instructions to perform operations to determine whether the change in the pulse rate has occurred between the two observation times by localizing pulses that occurred between the two observation times by one or more of:
   determining a zero crossing of a high-pass filter demodulated signal;
   localizing maximum pulse gradients;

localizing the pulses based on a quantity related to the maximum and minimum of each pulse; and
wavelet filtering to extract shape and time information.

* * * * *